United States Patent [19]

Clark

[11] Patent Number: 5,222,482
[45] Date of Patent: Jun. 29, 1993

[54] BINOCULAR ENDOSCOPE WITH DEPTH PERCEPTION AND FIXED FOCAL PLANE

[76] Inventor: Kenneth M. Clark, 3 Delantera Dr., Irvine, Calif. 92720

[21] Appl. No.: 684,838

[22] Filed: Apr. 15, 1991

[51] Int. Cl.⁵ .............................................. A61B 1/00
[52] U.S. Cl. .................................................... 128/4
[58] Field of Search .............. 128/4, 6; 359/367, 380, 359/383, 407, 410, 414, 421, 422, 432, 377; 385/117, 118

[56] References Cited

U.S. PATENT DOCUMENTS

| | | | |
|---|---|---|---|
| 3,485,584 | 12/1969 | Brebant et al. | 359/367 |
| 3,520,587 | 7/1970 | Tasaki et al. | 359/367 |
| 3,561,432 | 2/1971 | Yamaki et al. | 128/6 |
| 3,815,584 | 6/1974 | Fiore | 128/6 |
| 4,149,769 | 4/1979 | Zobel | 359/432 |
| 4,269,485 | 5/1981 | Yamashita et al. | 128/4 |
| 4,664,486 | 5/1987 | Landre et al. | 128/4 |
| 4,802,460 | 2/1989 | Ohkuwa et al. | 128/6 |
| 4,842,395 | 6/1989 | Sato et al. | 359/380 |

FOREIGN PATENT DOCUMENTS 0211113 12/1982 Japan ................................ 359/432
0586414 12/1977 U.S.S.R. ........................... 359/367

Primary Examiner—Gene Mancene
Assistant Examiner—Todd E. Manahan

[57] ABSTRACT

A binocular endoscope which uses a pair of coherent fiberoptic channels and associated objective lens systems which incorporate a "zoom" feature of magnification while preserving depth perception for the user. There are two longitudinally spaced lenses in each objective lens system. The endoscope is inserted into a body cavity and the object to be examined is brought into focus with the lenses separated at or near their minimum spacing in order to establish orientation within the body cavity. After orientation is established, the spacing between lenses is reset to be at or near its maximum distance between lenses and the scope is advanced axially to its fixed focal plane. Thereafter, the field of view and its concomitant magnification are varied without changing the axial position of the scope with respect to the patient.

6 Claims, 6 Drawing Sheets

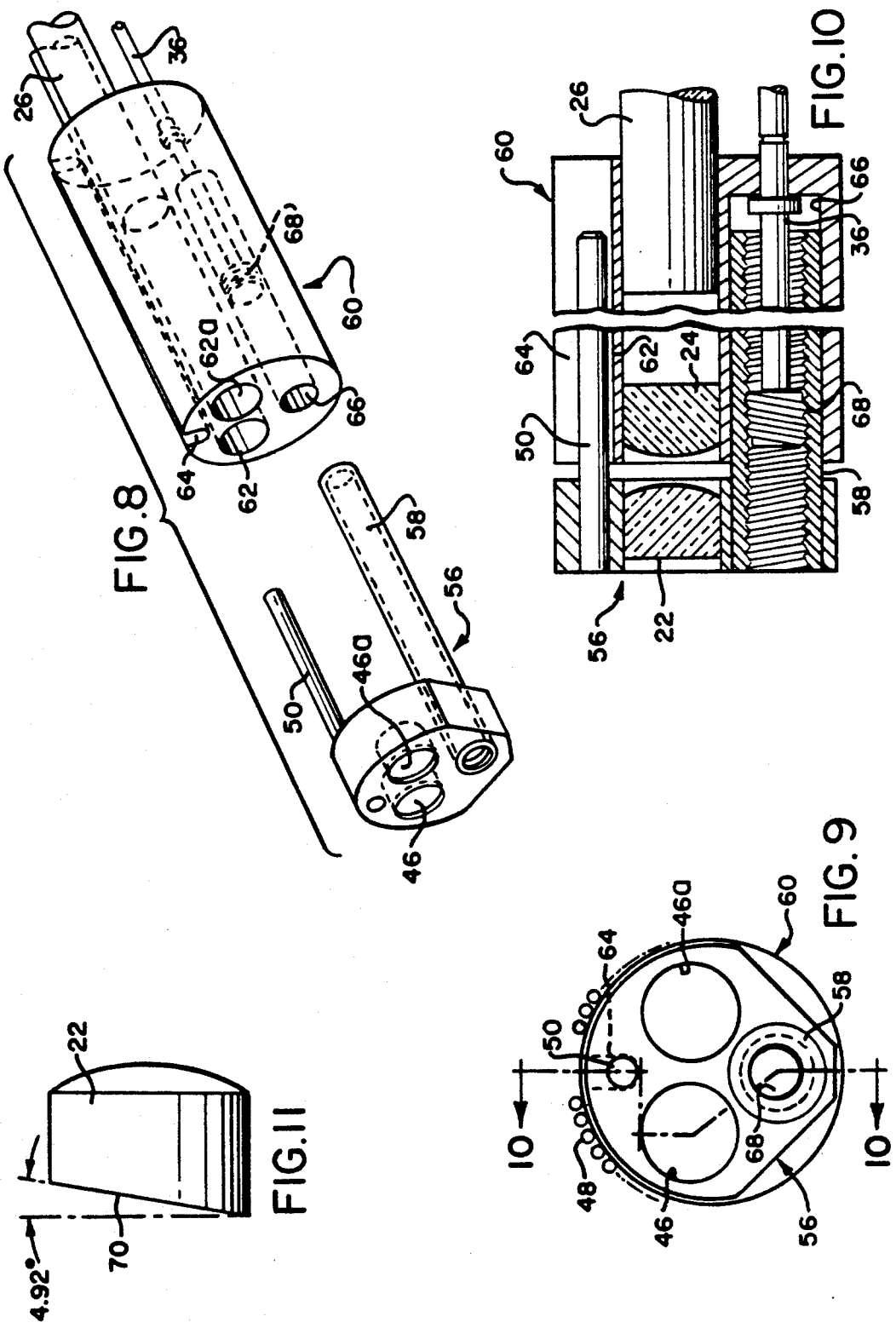

BINOCULAR ENDOSCOPE WITH DEPTH PERCEPTION AND FIXED FOCAL PLANE

This invention relates to a binocular endoscope and its method of use, and, more particularly, to a binocular endoscope which uses a pair of fiberoptic channels and an objective lens system which has a "zoom" feature of magnification while preserving depth perception for the user.

BACKGROUND OF THE INVENTION

Heretofore, attempts have been made to establish depth perception for endoscopes by using coextensive optical systems employing fiberoptics and relying upon the parallax angle between the two viewing paths to provide depth perception. U.S. Pat. Nos. 3,520,587 Tasaki et al and 4,061,135 Wildran et al are representative examples. Endoscopes of these types possess two unusual attributes. First, the image focus is universal, that is, it is independent of the distance from the distal tip of the endoscope. Second, the power of magnification is a product of distance so that magnification automatically increases with decreasing distance to the object. There are significant shortcomings in endoscopes of this type. One shortcoming is that the perception of distance becomes entirely dependent upon the viewer's prior knowledge of the size of the object being viewed. Another limitation is that in order to obtain increased magnification, the distal end of the endoscope must be advanced to a distance so close to the object being examined so as to risk touching or even puncture of the object. In a surgical environment this is not only dangerous, but intolerable.

SUMMARY OF THE INVENTION

In accordance with the present invention, the foregoing limitations and shortcomings are effectively overcome. In particular, an endoscope is provided with an objective lens system which is capable of changing magnification and concomitantly the field of view without changing the axial position of the endoscope with respect to the object in the patient's body that is being examined. This feature is extremely advantageous to the examining physician or user. It makes it possible to insert the endoscope into a body cavity of the patient with a first magnification and concomitant field of view setting in order to establish orientation with the body cavity. If desired, the endoscope may then be mounted on a stable holder or platform because thereafter, by decreasing the distance between the lenses of the objective lens system the user may increase the magnification without changing the axial position of the endoscope with respect to the patient. Whereas the prior art requires the surgeon to devote one hand to adjust axial position of the endoscope, the present invention eliminates the need for axial movement and reduces adjustments in magnification to the rotation of a knob which may easily be assigned to an assistant or be motorized. Since the axial position of the endoscope is not changed as magnification is increased, there is no danger of touching or puncturing the object being viewed as in prior art devices.

Through adjustments accomplished within the distal end of the instrument, the present invention accomplishes variations in the field of view consistent with the optical resolution requirements of increased magnification. In addition, the present invention provides a focus at a given and nearly constant distance forward of the distal end of the endoscope.

Two additional features of the binocular endoscope of the present invention are that the angle of convergence of the two fiberoptic channels is made consistent with the fixed focal plane and this distal angle of convergence is duplicated in the proximal eyepieces.

DEFINITIONS

Before beginning the detailed description of the invention there are a number of working definitions of terms that are used in the description of this invention that should be enumerated. These include the following:

Focal Plane

The image of an object located at the focal plane of an optical system is in perfect focus, meaning that the object is sharply defined. The image of objects at other distances from the distal tip of the instrument will be blurred to some extent. As the placement of an object departs from the focal plane, its image becomes increasingly blurred. When this blurring becomes objectionable, the object is said to be "out of focus". The "blur" numbers in the tables are mathematical means of predicting the blur associated with a given set of circumstances. Acceptable limits for calculated blur numbers may be established empirically for the present invention as indicated hereinafter.

Depth of Field

The range of distance for objects in acceptable focus is said to be the "depth of field" for a given adjustment of a lens system. Once calibrated, the blur numbers at the high and low ends of the range will predict the depth of field.

Field of View

Only a portion of a panorama is visible through a lens. The portion visible for a given setting of our system is the "field of view" for that setting. Typically, revision of the field of view are accompanied by revised distances between the viewed object and the instrument. The essence of the present invention is the ability to expand and contract the field of view without varying the distance to the object; i.e., the establishment of a "fixed focal plane" at which precision observation is accomplished.

Angle of Convergence

When viewing an object binocularly, a person's eyes automatically cant inwardly depending on the distance to the object being viewed so that the views of the two eyes overlap. This avoids "double vision". Our instrument has one, nonadjustable, angle of convergence which coincides with the "fixed focal plane". Departures from the fixed focal plane would immediately cause double vision were it not for the body's "dominant eye" mechanism. Experiments with a breadboard model indicate that the dominant eye will reliably correct for angular differences of plus/minus 4 degrees. The angle of convergence is used synonymously with the term "parallax angle".

Pistoning

A term which in conventional usage of endoscopes refers to the advance and retraction of the instrument within the body of a patient. Advancing the instrument results in increased magnification whereas retraction results in decreased magnification.

The inherent advantages and improvements of the present invention will become more apparent upon reference to the following detailed description of the invention and by reference to the accompanying drawings wherein:

BRIEF DESCRIPTION OF THE DRAWINGS

FIG. 8 is a fragmentary perspective view illustrating the means for effecting the zoom feature of the present invention;

FIG. 9 is an end elevational view of a holder for the movable objective lens;

FIG. 10 is a fragmentary side elevational view of the holder of FIG. 9 assembled with a holder for the stationary objective lens;

FIG. 11 is a side elevational view of a modified movable objective lens;

DETAILED DESCRIPTION OF THE INVENTION

Figure 1:
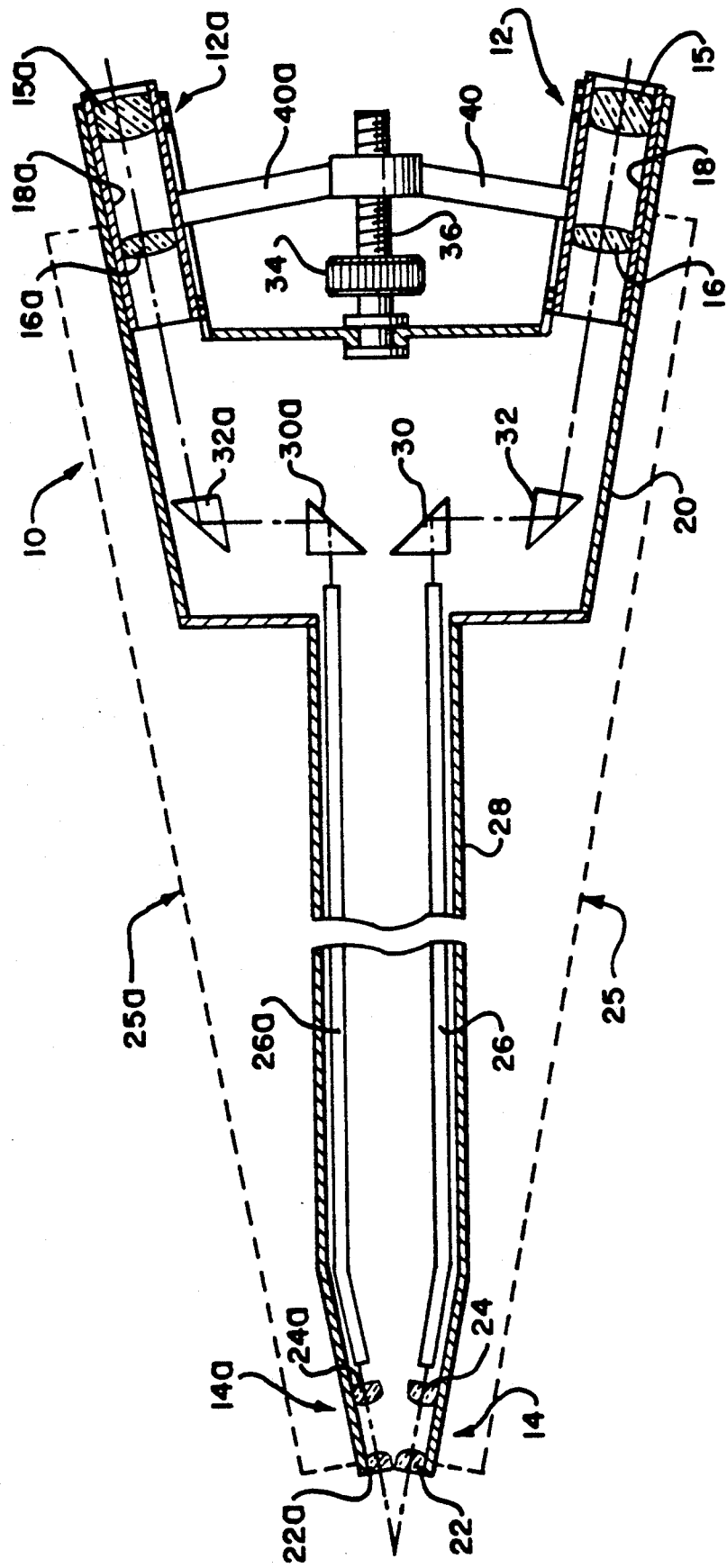
FIG. 1 is a top plan view taken partially in horizontal cross section and schematically showing one embodiment of a binocular endoscope of this invention.

Referring now to FIG. 1 of the drawings, a binocular endoscope in schematic form is indicated generally at 10. The binocular endoscope has two parallel viewing paths only one of which will be described with the same numeral followed by the letter "a" used to designate corresponding elements in the parallel viewing path.

An eyepiece lens system is indicated generally at 12 and an objective lens system is designated generally at 14. An eyepiece lens 15 and an erector lens 16 are included in the eyepiece lens system each mounted in a sleeve 18 which is slidably mounted in a tubular extension of main frame 20. The erector lens 16 inverts the image for proper viewing by the user.

The objective lens system includes a movably mounted objective lens 22 and a slightly more proximately positioned and fixedly mounted objective lens 24. The means for moving distally positioned objective lens 22 in concert with the eyepiece lens system is schematically represented by numeral 25 in FIG. 1. The details of effecting the movement of lens 22 is shown in FIGS. 8–10 and will be described in greater detail hereinafter.

A coherent fiberoptic channel 26 is positioned behind the stationary objective lens 24 and contained within an elongated sheath 28. The fiberoptic channels employed can be in either a semirigid or flexible form. In the breadboard model used to prove the feasibility of the present invention, the distal ends of the fiberoptic channels were formed or bent inwardly as shown in FIG. 1 so as to be in line with the tubular extensions of main frame 20 which contains the eyepiece lens system in spite of the circuitous route taken by the fiberoptics employed. The image transported by the coherent fiberoptic channel 26 are refracted and redirected by prisms 30, 32 to the eyepiece lens system 12.

One schematic means for effecting movement of sleeve 18 in the eyepiece lens system 12 is by turning a control knob 34 which is fixed to shaft 36 to cause reciprocation of an internally threaded hub 38 on shaft 36. Links or control arms 40 suitably attached to sleeve 18 causes limited sliding movement thereof within the tubular extensions of main frame 20.

Figure 2:
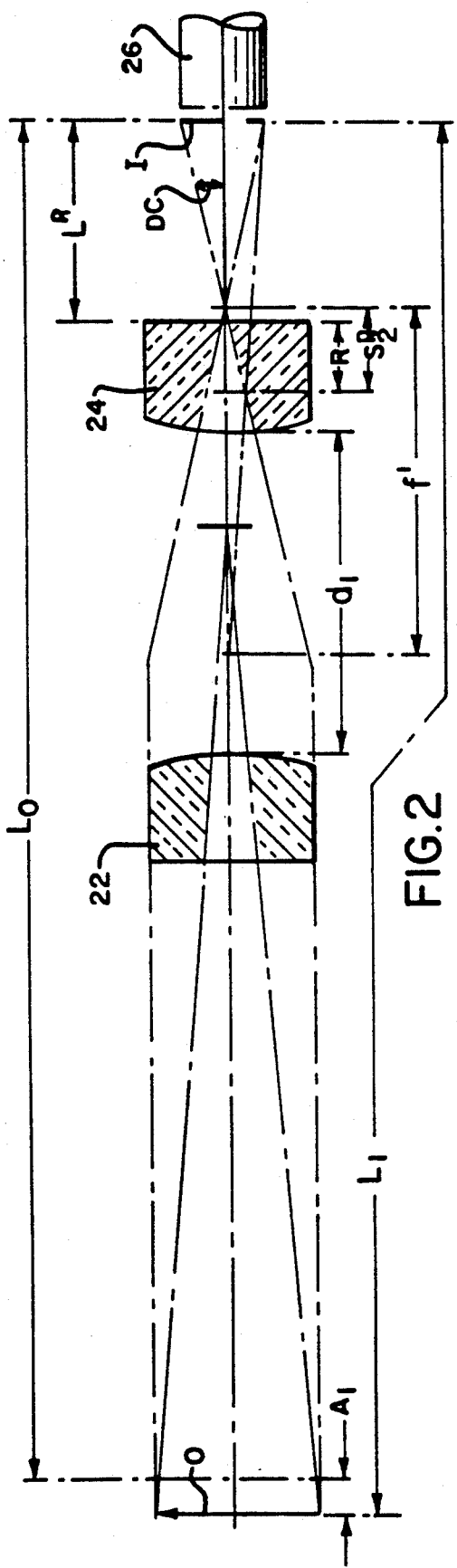
FIG. 2 is a fragmentary schematic view, drawn to an enlarged scale, of the objective lens system of FIG. 1.
Figure 3:
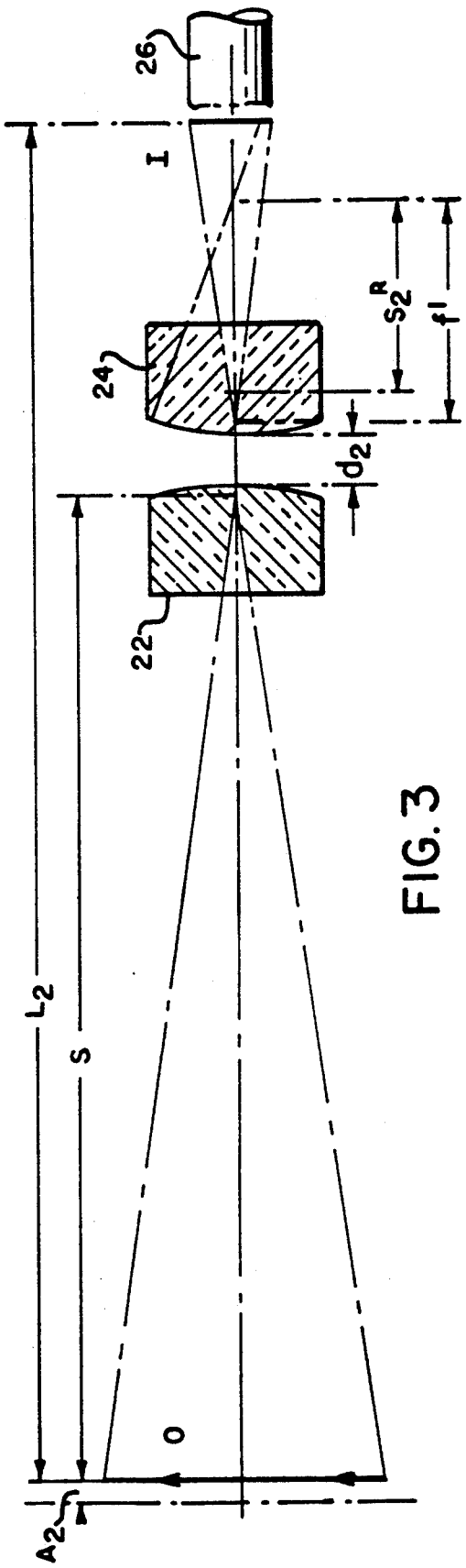
FIG. 3 is a fragmentary schematic view of the objective lens system of FIG. 2 but illustrating a different lens setting.
Figure 4:
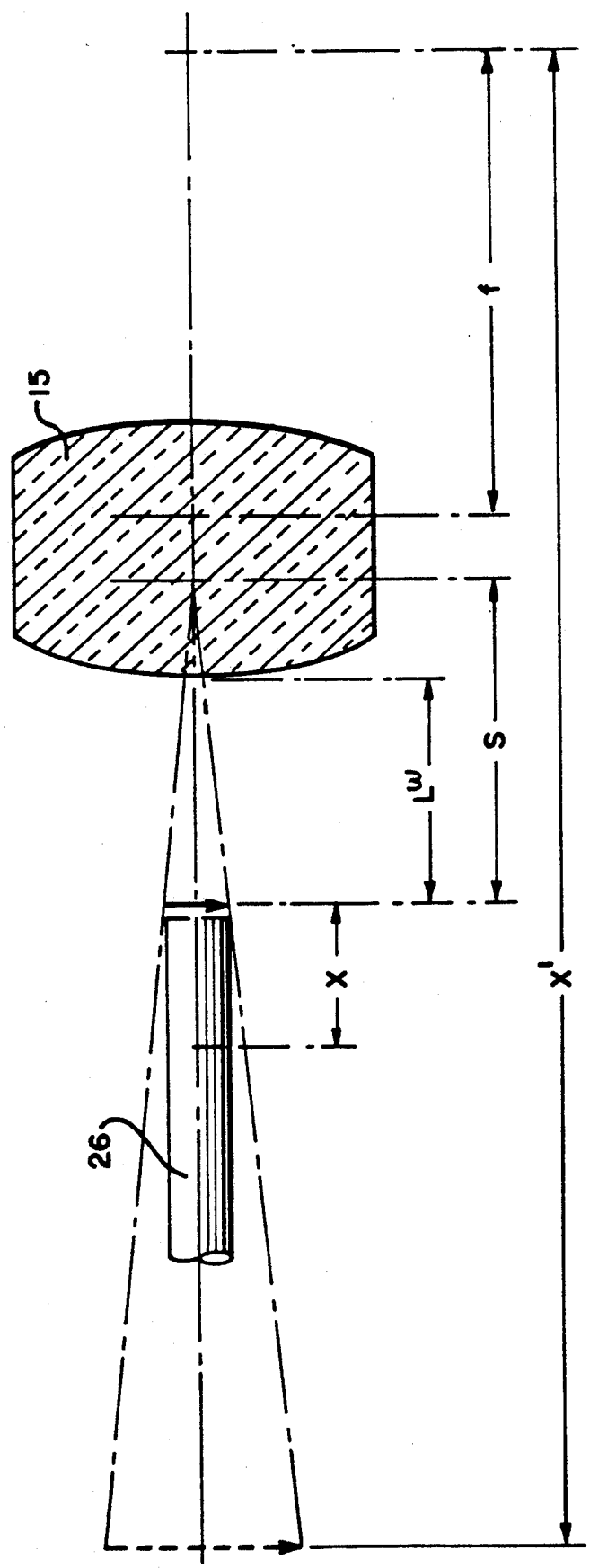
FIG. 4 is a fragmentary schematic view of the eyepiece of FIG. 1 with portions removed and applicable to a breadboard only.

Turning now to FIGS. 2 and 3 of the drawings, two different settings or spacings are shown between fixed lens 24 and movable lens 22. The following dimensional and spatial relationships are illustrated and designated in FIGS. 2–4 and computer calculations made therefrom using conventional optics formulae:

d = the distance in millimeters between objective lenses 22, 24.

$\alpha$ = the angle in degrees between the centerline for lenses 22, 24 and a ray passing through the rear focal point for lenses 22, 24.

$f_o$ = the focal length in millimeters of each lens 22, 24 acting separately.

f' = the focal length in millimeters of lenses 22, 24 acting in unison and is given by the following formula:

$$f' = \frac{f_o^2}{2f_o - d}$$

n = the distance in millimeters for lens 24 between its rear principal point and its rear surface.

L = the calculated distance in millimeters between the focal plane and the image formed on the distal end of the fiberoptic channel with the distance d being defined as the distance between lenses 22, 24. For example, $L_1$ corresponds to $d_1$.

$L_o$ = the distance in millimeters between the focal plane for a base setting for objective lenses 22, 24 and the distal end of fiberoptic channel 26. $L_o$ determines the apex of parallax angle.

$s_2''$ = the distance in millimeters between the rear principal point of lens 22 and the rear focal point for lenses 22, 24 acting in unison and is given by the following formula:

$$s_2'' = \frac{f_o (f_o - d)}{2f_o - d}$$

L''—the distance in millimeters between the rear face of fixed lens 24 and the distal face of fiberoptic channel 6.

L‴ = the distance in millimeters between the proximal end of fiberoptic channel 26 and the leading surface of eyepiece 15 applicable to breadboard only.

s″ = the image distance in millimeters for use in describing this invention and is given by the following formula:

$$s'' = f - s_2'' + n + L''$$

s = the distance in millimeters from the object to the principal point of a lens combination being used and is given by the following formula:

$$s = \frac{fs''}{s'' - f}$$

$\Delta_1$ = the distance in millimeters representing a small deviation from the nominal convergence of the center lines of the views presented to the eyes of the viewer and the dimension $L_1$ for a given separation $d_1$.

$\Delta_2$ = the distance in millimeters representing a small deviation from the nominal convergence of the center lines of the views presented to the eyes of the viewer and the dimension $L_2$ for a second separation $d_2$.

m = magnification and is a ratio of the size of the image to the size of the object. It may also be expressed as the ratio of the image distance s divided by the object distance.

x = the distance in millimeters from the forward focal point for lens 15 to the proximal end of the fiberoptic channel 26. (Applicable to the breadboard only.)

f = the distance in millimeters for the focal length of eyepiece lens 15 (applicable to the breadboard only).

x′ = the distance in millimeters to the magnified virtual image wherein the following basic equations are employed (applicable to the breadboard only):

$$m = \frac{f}{x}$$

$$x' = \frac{f^2}{x}$$

Using various spacing between lenses 24, 26, a fixed spacing L″ = 3.75; n = 1.3; yields $L_o$ = 25.34 and the following results were obtained as set forth in table 1.

All dimensions in this specification are given in millimeters.

TABLE 1

| d | f | s″ | m | $\Delta L_o$ |
|---|---|---|---|---|
| 0.5 | 4.13 | 5.3 | 0.29 | −0.06 |
| 1.0 | 4.27 | 5.6 | 0.31 | −0.33 |
| 1.5 | 4.41 | 5.9 | 0.33 | −0.49 |
| 2.0 | 4.57 | 6.2 | 0.35 | −0.57 |
| 2.5 | 4.74 | 6.5 | 0.38 | −0.58 |
| 3.0 | 4.92 | 6.9 | 0.40 | −0.53 |
| 3.5 | 5.12 | 7.3 | 0.42 | −0.43 |
| 4.0 | 5.33 | 7.7 | 0.45 | −0.29 |
| 4.5 | 5.57 | 8.2 | 0.47 | −0.11 |
| 5.0 | 5.82 | 8.7 | 0.49 | 0.09 |
| 5.5 | 6.10 | 9.2 | 0.52 | 0.33 |
| 6.0 | 6.40 | 9.9 | 0.54 | 0.58 |

The depth of field which is a function of the blur numbers was investigated using d = 6.0 mm, f = 6.40 mm and a field of view = 2.97 mm to yield the following results:

TABLE 2

| L | BLUR NUMBERS |
|---|---|
| −1.00 | −0.0312 |
| −0.75 | −0.0231 |
| −0.50 | −0.0152 |
| −0.25 | −0.0075 |
| 0.00 | 0.0000 |
| 0.25 | 0.0073 |
| 0.50 | 0.0144 |
| 0.75 | 0.0213 |
| 1.00 | 0.0280 |

The invention has been developed using blur numbers which include positive and negative numbers rather than blur diameters. The use of blur numbers has been useful in the development of the invention because the positive and negative sign indicated on which side of the fixed focal plane the virtual image appears. To convert to blur diameters, you eliminate the sign and double the number.

It has been determined empirically that when using the binocular endoscope of the present invention in the fixed focal plane mode, that satisfactory vision is provided when the diameters do not exceed 0.040 mm for the largest value for m and 0.076 mm for the smaller values of m. When using the binocular endoscope in the conventional or pistoning mode in which the endoscope is moved into or out of the human body cavity to change magnification, satisfactory viewing at the eyepiece is provided when the blur diameter does not exceed 0.140 mm at the greater distance and 0.100 mm at the shorter distance.

One of the essential improvements of the present invention is that it is possible to select a value for L″ such that a value for $L_o$ is found which remains substantially unchanged even though the spacing between lenses 22 and 24 is varied. Thus, the end result is that a proper choice for L″ results in the establishment of a substantially fixed focal plane in front of the distal end of the endoscope. From an operating standpoint this means that the surgeon may insert the binocular endoscope with a particular setting for the distance between lenses that gives a wide field of view. The surgeon may then secure that axial position for the endoscope such as by mounting on a stand or suitable holder. The surgeon then changes the spacing between lenses 22, 24 namely increasing the distance to obtain greater magnification without changing the axial position for the endoscope.

It has been found unexpectedly, that in order to obtain a substantially fixed focal plane, the more distal lens 22 must be moved and the more proximal lens 24 kept stationary. When the reverse was tried, that is, maintaining the distal lens 22 stationary and more proximal lens 24 movable, no fixed focal plane could be found.

The second advantage which accrues to the user of the endoscope of the present invention is that because there is a predetermined and relatively fixed distance between the distal tip of the instrument and the fixed focal plane, which applies for multiple powers of magnification, the user can be assured of a known separation between his instrument and the body structure under observation. Consequently, the risk of inadvertently touching or puncturing the body structure is substantially reduced or eliminated. A third advantage which accrues is the opportunity to provide a comfortable working distance for the insinuation and negotiation of medical instruments appropriate for differing surgical specialties.

In order to demonstrate that depth perception is achieved in the endoscope of the present invention, the following experiment was performed. A guide piece which carries a vertical pin No. 1 was used in conjunction with a slide piece which carried a vertical pin No. 2. The guide piece was positioned so as to locate pin No. 1 at the focal plane and within the field of view. Contact between the guide and slide was such that pin No. 2 could be moved away from or nearer to the observer without other than visual indication of alignment opposite pin No. 1. The perception of depth on the part of the observer allows him to determine when the pin No. 2 has been adjusted to the same distance from the tip of the instrument as pin No. 1 which remains fixed during the experiment. Using the breadboard established for FIGS. 1–4, it was possible to position pin No. 2 repeatedly to within ±0.1 mm of perfect alignment of the two pins.

Figure 5:
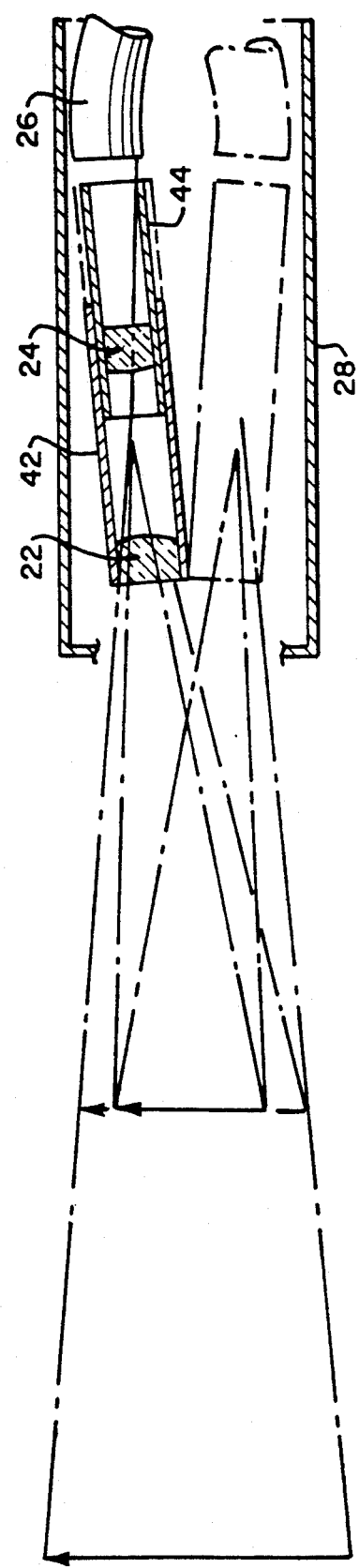
FIG. 5 is a fragmentary plan view taken in horizontal cross section through the sheath of an endoscope showing another embodiment.

Referring now to FIG. 5 of the drawings, movable lens 22 is illustrated to be mounted in a telescoping slide member 42 so that it may be moved with respect to fixed lens 24. It will be observed that slide member 42 and holder 44 for the fixed lens are tilted toward the center axis of elongated sheath 28 which in this embodiment does not taper inwardly as in FIG. 1. However, this tilting of the members 42, 44 makes it more difficult to meet the desired objective of an endoscope having a diameter of 4 mm so that this concept was discarded.

Figure 7:
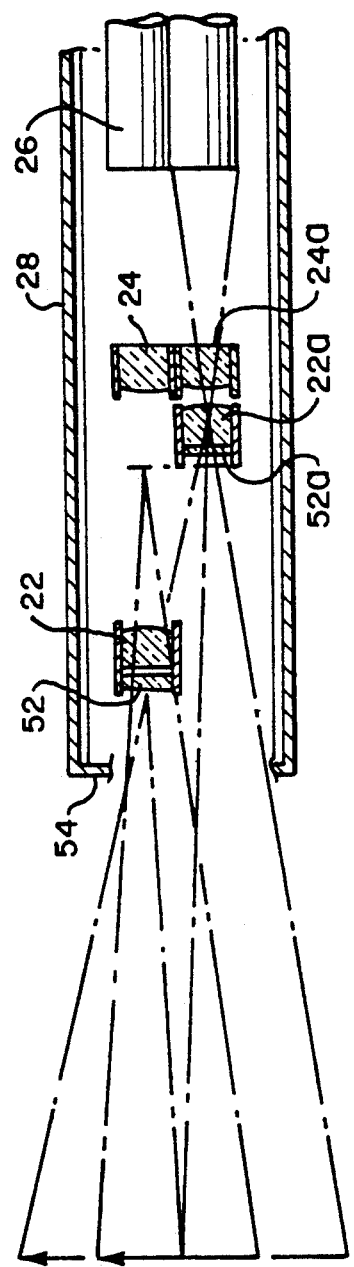
FIG. 7 is a fragmentary plan view of the endoscope of FIG. 6 taken in horizontal cross section with parts removed.
Figure 6:
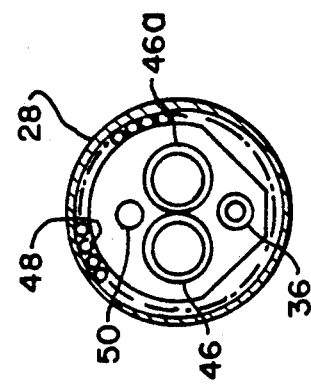
FIG. 6 is an end elevation view of an endoscope showing a further embodiment of the invention.

FIGS. 6 and 7 show an improved embodiment wherein suitable carriers or sockets 46 are shown for the lens members and a ring of fiberoptic channels 48 encircle the distal tip adjacent the inside diameter of sheath 28. These fiberoptic channels 48 provide additional illumination for the object being examined within a human body cavity. FIG. 7 also illustrates wedge shaped prisms 52 which are designed to provide for the parallax angle or angle of convergence inherent in two side by side viewing channels. This further facilitates the use of a sheath member having a constant external diameter and is the preferred embodiment for the sheath member. In addition, a straight-walled sheath greatly simplifies the mechanisms required to effect the zoom feature between objective lenses 22, 24 and the concomitant movement of the eyepiece lens system 12. The wedge-shaped prism members 52 are shown positioned behind window 54 which is clear glass to seal off the distal end of the endoscope. FIG. 6 also discloses an anti-rotation guide means 50 which takes the form of a pin member shown more clearly in FIGS. 8–10. In FIG. 7, lenses 22, 24 are illustrated with a separation d=7.5 mm and lenses 22a, 24a are illustrated with a 0.50 mm separation.

Referring now to FIGS. 8–10, a carrier is indicated generally at 56 with a socket 46 for movable objective lens 22 and two rearwardly extending members in the form of guide pin 50 and internally threaded support tube 58. A holder is indicated generally at 60 for the stationary objective lens 24 which is fixedly retained in socket 62. Holder 60 is provided with a groove or bore to receive guide pin 50 thereby providing a cantilevered and non-rotating mounting for carrier 56 for the movable objective lens 22. Holder 60 is also provided with bore 66 for the internally threaded support tube 58. Shaft 36 is provided with an enlarged threaded head 68 at its distal end for engagement with the internal threads of support tube 58. Therefore, rotation of shaft 36 by means of control knob 34 of FIG. 1 not only produces either advancing or retrograde movement of holder 56 for movable objective lens 22, but also produces concomitant movement of the eyepiece lens system 12 of FIG. 1.

In FIG. 11, movable objective lens 22 is illustrated to have its most distal face provided with a bevel of 4.92 degrees in order to compensate for the parallax angle. Thus, this lens 22 may be placed in socket 46 of FIG. 8 and used in the embodiment of FIG. 10.

While a preferred usage of the endoscope of the present invention is its use with the selection of L" distances to yield a substantially fixed focal plane as evidenced by relatively small delta L numerals, it is possible to use the endoscope in a so-called pistoning mode. Additional care in the choice of L" results in an instrument which may also be used in the conventional or pistoning manner, that is, by advancing or retracting the instrument to produce variations in the field of view. Of course, this is especially useful in the initial insertion of the endoscope into a cavity of the human body as the endoscope approaches the position in which it reaches the fixed focal plane.

For example, using the embodiment of FIG. 7, a fixed focal plane was established 15.0 mm in front of the distal end of the endoscope which had a diameter of 12.5 mm. A L" dimension of 5.80 was selected providing an $L_o$ 43.518 mm. The effective focal length ($F_o$) for each objective lens equal 12.5 mm. An overhang of 4.118 mm was provided which is the distance that the sheath 28 extends beyond the base setting of 14.20, thus providing space for the largest expected separation to be used between lenses 22, 24, in this instance 16.2 mm. These settings yielded the following results:

TABLE 3

| SET | m | FLD | BLUR NUMBER |
| --- | --- | --- | --- |
| 0.20 | 0.17 | 15.0 | −0.0385 |
| 1.20 | 0.21 | 13.8 | −0.0236 |
| 2.20 | 0.24 | 12.7 | −0.0103 |
| 3.20 | 0.27 | 11.7 | 0.0014 |
| 4.20 | 0.31 | 10.8 | 0.0114 |
| 5.20 | 0.34 | 9.9 | 0.0194 |
| 6.20 | 0.37 | 9.1 | 0.0255 |
| 7.20 | 0.41 | 8.4 | 0.0294 |
| 8.20 | 0.44 | 7.8 | 0.0313 |
| 9.20 | 0.47 | 7.2 | 0.0310 |
| 10.20 | 0.51 | 6.7 | 0.0286 |
| 11.20 | 0.54 | 6.2 | 0.0240 |
| 12.20 | 0.57 | 5.7 | 0.0176 |
| 13.20 | 0.61 | 5.3 | 0.0095 |
| 14.20 | 0.64 | 5.0 | 0.0000 |
| 15.20 | 0.67 | 4.7 | −0.0103 |
| 16.20 | 0.71 | 4.4 | −0.0210 |

With the same parameters as in table 3 and a setting of 0.20 mm between lenses 22, 24, the following field, angle of convergence and blur numbers were obtained at the designated distances in front of the endoscope:

TABLE 4

| | PISTONING MODE | | |
| --- | --- | --- | --- |
| DIST. | FLD | Δ OF C | BLUR NUMBER |
| 50 | 30.0 | 3.7 | 0.0685 |
| 45 | 27.9 | 4.1 | 0.0603 |
| 40 | 25.7 | 4.6 | 0.0507 |
| 35 | 23.6 | 5.2 | 0.0394 |
| 30 | 21.4 | 6.1 | 0.0258 |
| 25 | 19.3 | 7.3 | 0.0092 |
| 20 | 17.1 | 9.2 | −0.0117 |
| 15 | 15.0 | 12.2 | −0.0385 |
| 14 | 14.5 | 13.1 | −0.0448 |
| 13 | 14.1 | 14.1 | −0.0515 |

Using a 4.0 mm diameter endoscope and the arrangement shown in FIG. 10, an 18.50 mm fixed focal plane was established using $f_o = 10.000$ mm and $L'' = 5.600$ mm. This provided an overhang of 1.356 mm and yielded the following results:

TABLE 5

| SET. | m | FLD | BLUR NUMBER |
|---|---|---|---|
| 0.25 | 0.21 | 8.0 | −0.03622 |
| 1.00 | 0.24 | 7.4 | −0.02602 |
| 1.75 | 0.27 | 6.8 | −0.01738 |
| 2.50 | 0.30 | 6.3 | −0.01036 |
| 3.25 | 0.33 | 5.8 | −0.00508 |
| 4.00 | 0.36 | 5.4 | −0.00160 |
| 4.75 | 0.39 | 5.0 | 0.00000 |
| 5.50 | 0.42 | 4.7 | −0.0003 |
| 6.25 | 0.45 | 4.3 | −0.0026 |

Using a setting of 0.25 for the distance between lenses 22, 24 and the remaining parameters as established for table 5, the following values were obtained:

TABLE 6

| DIST. | FLD | Δ OF C | BLUR DIAMETER |
|---|---|---|---|
| 35 | 13.2 | 2.3 | 0.1239 |
| 30 | 11.6 | 3.2 | 0.0832 |
| 25 | 10.0 | 3.9 | 0.0296 |
| 20 | 8.4 | 4.9 | 0.0444 |
| 19 | 8.1 | 5.1 | 0.0627 |
| 18 | 7.8 | 5.4 | 0.0825 |
| 17 | 7.5 | 5.7 | 0.1040 |

In order to exploit the variations in the field of view offered by the adjustable objective lens system of the present invention, the control of the distal end of the scope has been coupled directly to the adjustable eyepiece magnification mechanism of the proximal end of the instrument. Table 7 which follows, provides an example of this coupling to an eyepiece adjustable between magnifications between 4X and 22X. The resulting overall magnification of the distal and proximal optics range between 0.7X and 15.4X, thereby providing the user with a zoom effect.

TABLE 7

| | POWER (X) | | | |
|---|---|---|---|---|
| NO. | FLD | OBJ | EP | TOT |
| 1 | 15.0 | 0.17 | 4.0 | 0.7 |
| 2 | 13.1 | 0.23 | 6.0 | 1.4 |
| 3 | 11.4 | 0.29 | 8.0 | 2.3 |
| 4 | 10.0 | 0.35 | 10.0 | 3.5 |
| 5 | 8.7 | 0.41 | 12.0 | 4.9 |
| 6 | 7.6 | 0.47 | 14.0 | 6.5 |
| 7 | 6.6 | 0.52 | 16.0 | 8.4 |
| 8 | 5.8 | 0.58 | 18.0 | 10.5 |
| 9 | 5.0 | 0.64 | 20.0 | 12.8 |
| 10 | 4.4 | 0.70 | 22.0 | 15.4 |

The end result of selectively decoupling the distal and proximal optics are illustrated in Tables 8 and 9 which follow. Ranges between 2.4X and 9.8X with fields ranging from 15.0 mm to 4.4 mm, and between 1.7X and 9.5X with an 8.2 mm field, are obtainable in this manner each providing differing perceptions of zoom. The latter decoupled results are best accomplished using servomotors, not shown. It may also be accomplished with a disconnect lever and separate locks, or brakes, for a manual mode device.

TABLE 8

| | POWER (X) | | | |
|---|---|---|---|---|
| NO. | FLD | OBJ | EP | TOT |
| 1 | 15.0 | 0.17 | 14.0 | 2.4 |
| 2 | 13.1 | 0.23 | 14.0 | 3.2 |
| 3 | 11.4 | 0.29 | 14.0 | 4.1 |
| 4 | 10.0 | 0.35 | 14.0 | 4.9 |
| 5 | 8.7 | 0.41 | 14.0 | 5.7 |
| 6 | 7.6 | 0.47 | 14.0 | 6.5 |
| 7 | 6.6 | 0.52 | 14.0 | 7.3 |
| 8 | 5.8 | 0.58 | 14.0 | 8.1 |
| 9 | 5.0 | 0.64 | 14.0 | 9.0 |
| 10 | 4.4 | 0.70 | 14.0 | 9.8 |

TABLE 9

| | POWER (X) | | | |
|---|---|---|---|---|
| NO. | FLD | OBJ | EP | TOT |
| 1 | 8.2 | 0.43 | 4.0 | 1.7 |
| 2 | 8.2 | 0.43 | 6.0 | 2.6 |
| 3 | 8.2 | 0.43 | 8.0 | 3.5 |
| 4 | 8.2 | 0.43 | 10.0 | 4.3 |
| 5 | 8.2 | 0.43 | 12.0 | 5.2 |
| 6 | 8.2 | 0.43 | 14.0 | 6.1 |
| 7 | 8.2 | 0.43 | 16.0 | 6.9 |
| 8 | 8.2 | 0.43 | 18.0 | 7.8 |
| 9 | 8.2 | 0.43 | 20.0 | 8.7 |
| 10 | 8.2 | 0.43 | 22.0 | 9.5 |

Figure 12:
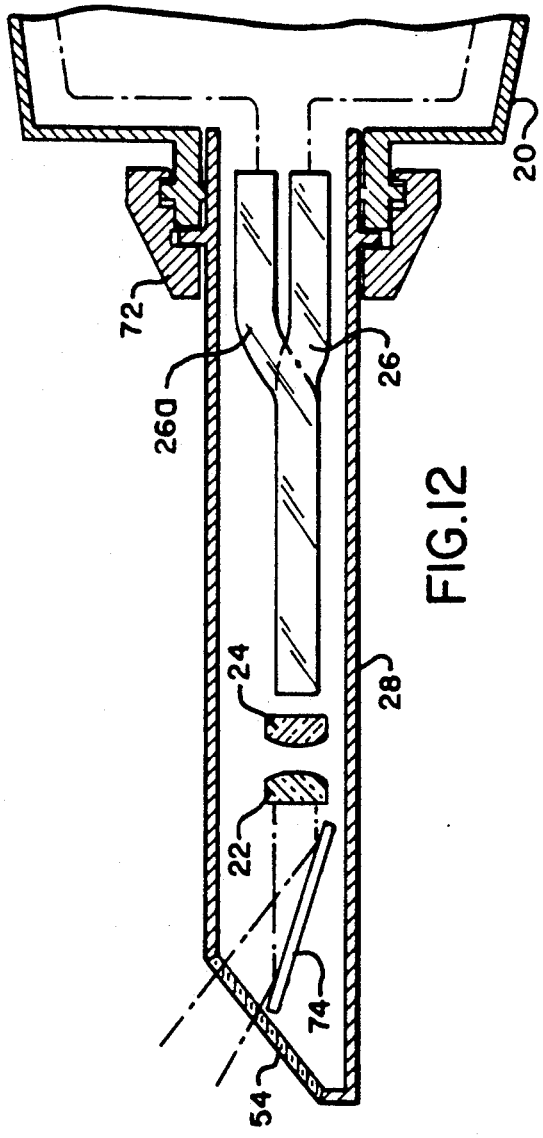
FIG. 12 is a top plan of a modified endoscope having an interchangeable distal tip.

To enhance the versatility of the basic embodiment, particularly during use in surgery, two means of viewing objects laterally are employed. As is illustrated in FIG. 12, one embodiment employs a static mirror or prism 74 for viewing at a fixed lateral angle, be the angle 30, 60, 90 or 120 degrees. To provide versatility to the instrument, the coupling 72 for the distal appendages is of a quick disconnect style to facilitate interchangeability from straight ahead viewing to the various lateral angles available.

Figure 13:
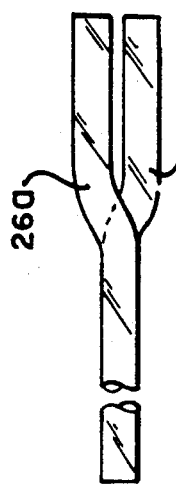
FIG. 13 is a top plan view illustrating a 90 degree twist for rigid fiberoptic channels.

FIG. 12 shows an appendage for sheath 28 with mirror or prism 74 set for 30 degrees and window 54 positioned to accommodate this angle. With the aid of the quick disconnect 72, it is possible to provide two orientations of this interchangeable distal portion of the invention so that viewing may be either to the left or the right using the same appendage. FIG. 13 indicates a 90 degree twist in the fiberoptic conduits needed to accomplish left or right viewing. Up or down deflection of the line of sight is accomplished with similar placement of the mirror but does not require the 90 degree twist of the conduits.

Figure 14:
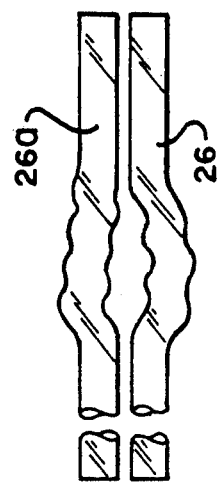
FIG. 14 is a top plan view illustrating flexible fiberoptic channels.

Whereas FIG. 13 indicates two fiberoptic channels fabricated with a rigid 90 degree twist, FIG. 14 indicates a flexible section of optical conduit which allows intermediate rotations from looking up to looking down.

Figure 15:
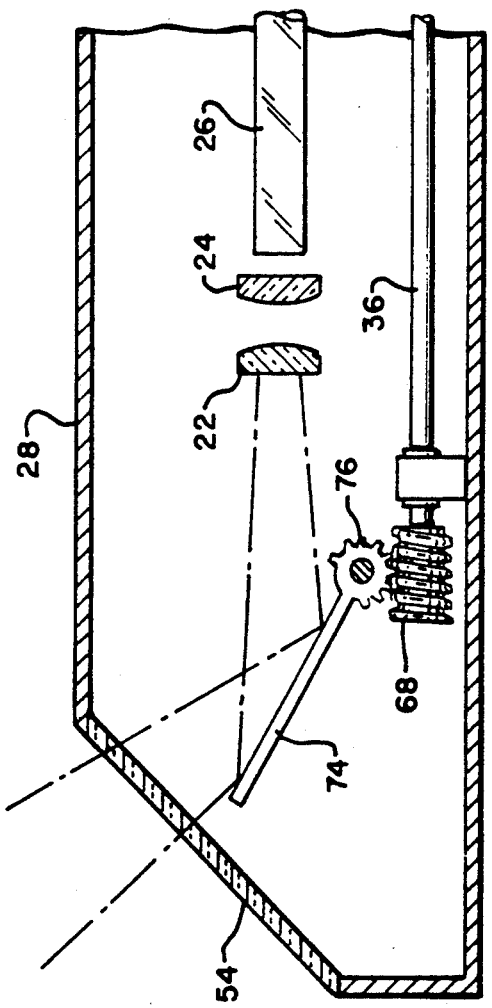
FIG. 15 is a side elevational view of a modified form of the invention.

FIG. 15 provides a means for employing an adjustable mirror 74 controlled by a toothed pawl member 76 for viewing at all intermediate angles between 15 and 120 degrees of lateral viewing. Combined with the flexible conduit of FIG. 14, this adjustable mirror 74 provides a rotating lateral field of view.

While the invention has been developed primarily for endoscopes which are binocular in nature to provide depth perception, the aspect of viewing an object with one setting of the objective lenses and being able to change the magnification and field of view without axial movement of the endoscope has applications in monocular endoscopes as well.

Two alternatives to the use of coherent fiberoptic channels are available from conventional optic systems. These are, first, the use of a system of relay lenses wherein each viewing path is provided with a series of lenses to transmit the image to an eyepiece lens which is used in combination with the adjustable objective lens system of the present invention. The second alternative is to use a collimating lens system in combination with the adjustable objective lens system disclosed herein for presentation of an image to the eyepiece lens of a viewer.

While presently preferred embodiments of the invention have been illustrated and described, it will be recognized that the invention may be otherwise variously embodied and practiced within the scope of the claims which follow.

We claim:

1. A binocular endoscope having a pair of viewing paths with a separate objective lens system and eyepiece lens system for each viewing path, comprising:

the objective lens system includes first and second lenses arranged along the viewing path with the first lens being located closer to the eyepiece lens system than the second lens; and means interconnecting the second lens of each objective lens system with a separate eyepiece lens system for adjusting the eyepiece lens systems and second lenses as a unit with respect to the first lens to achieve magnification change.

2. A binocular endoscope as in claim 1, in which first and second coherent fiberoptic channel are respectively located along each viewing path for transmitting light from the objective lens systems to the eyepiece systems.

3. A binocular endoscope as in claim 1, in which each eyepiece lens system includes an eyepiece lens and an erector lens.

4. A binocular endoscope as in claim 1, in which the two second lenses are mounted within a socket and the two first lenses are mounted within a holder, said socket including a guide pin and internally threaded support tube which are slidingly received within separate bores in the holder; a rotatable shaft with an enlarged threaded head that is threaded within the support tube which shaft on rotating effects an adjustment of the spacing between the first and second objective lens systems lenses.

5. A binocular endoscope as in claim 1, in which there are further provided separate prism means optically adjacent each second lens to correct for the parallax angle in side-by-side viewing paths.

6. A binocular endoscope as in claim 1, in which the focal plane is a fixed determinable distance from the objective lens system first lens outwardly beyond the second lens.

* * * * *